(12) United States Patent
Chen et al.

(10) Patent No.: US 8,574,906 B2
(45) Date of Patent: Nov. 5, 2013

(54) CELL CULTURE SURFACES HAVING HYDROGEL SUPPORTED PROTEINS

(75) Inventors: Xiaoxi (Kevin) Chen, Westborough, MA (US); Susan X. Qian, Concord, MA (US)

(73) Assignee: Corning Incorporated, Corning, NY (US)

(*) Notice: Subject to any disclaimer, the term of this patent is extended or adjusted under 35 U.S.C. 154(b) by 780 days.

(21) Appl. No.: 12/188,477

(22) Filed: Aug. 8, 2008

(65) Prior Publication Data

US 2009/0043079 A1    Feb. 12, 2009

Related U.S. Application Data

(60) Provisional application No. 60/954,916, filed on Aug. 9, 2007.

(51) Int. Cl.
*C12N 5/00* (2006.01)
*C12N 5/02* (2006.01)

(52) U.S. Cl.
USPC ............ 435/402; 435/395; 435/397

(58) Field of Classification Search
USPC ............ 435/402, 395, 397
See application file for complete search history.

(56) References Cited

U.S. PATENT DOCUMENTS

| | | | |
|---|---|---|---|
| 2004/0062882 A1* | 4/2004 | Liebmann-Vinson et al. | 428/34.1 |
| 2005/0154534 A1* | 7/2005 | Haaland et al. | 702/19 |
| 2007/0184295 A1* | 8/2007 | Chen et al. | 428/524 |

OTHER PUBLICATIONS

Leach et al. J. Biomed. Mater. Res., 70A: 74-82, 2004.*
Nuttelman et al., J. of Biomed. Mater. Res., 57: 217-223, 2001.*
dos Reis et al., Materials Research, 9(2):185-191, Jun. 2006.*
Levesque et al., Biomaterials, 27: 5277-5285, 2006.*

* cited by examiner

*Primary Examiner* — Thaian N Ton
(74) *Attorney, Agent, or Firm* — Hoffmann & Baron, LLP

(57) ABSTRACT

A method is disclosed herein for treating a polymeric surface to define an improved cell culture surface. The method includes the steps of: coating the polymeric surface with a hydrogel; and attaching proteins to the hydrogel-coated surface. Advantageously, a method is provided which consistently produces improved cell culture surfaces that generally avoid bare spots and possible undesired protein absorption or cell differentiation.

9 Claims, 3 Drawing Sheets

_US 8,574,906 B2_

CELL CULTURE SURFACES HAVING HYDROGEL SUPPORTED PROTEINS

CROSS-REFERENCE TO RELATED APPLICATION

This application claims priority to U.S. Provisional Patent Application No. 60/954,916, filed Aug. 9, 2007, the entire contents of which are hereby incorporated by reference.

FIELD OF THE INVENTION

The present invention relates to methods of treating polymeric surfaces with hydrogel supported proteins, for improved cell culture, and surfaces prepared by the same.

BACKGROUND OF THE INVENTION

Bare plastic surfaces, such as polystyrene surfaces, typically do not provide a sufficient surface for growth of cell cultures. The incorporation of proteins on plastic surfaces helps to enhance adhesion and growth of cell cultures. In the prior art, such protein incorporation has been performed using passive coating of proteins on the surfaces. Passive coating, however, is known to have several problems, including denaturing, due to the change from a solution environment to a surface confined environment, and desorbing of coated proteins from the surface during cell culture, leaving bare spots. Passive absorption typically requires higher protein concentration in solution, likely due to low percentage of bound protein that has correct confirmation or orientation for cell adhesion. Bare spots oil the surface may undesirably absorb proteins from the cell cultures. In addition, bare spots may result in the undesired direct attachment of the cells on the bare plastic surface, resulting in possible cell differentiation.

SUMMARY OF THE INVENTION

A method is disclosed herein for treating a polymeric surface to define an improved cell culture surface. The method includes the steps of: coating the polymeric surface with a hydrogel; and attaching proteins to the hydrogel-coated surface. Advantageously, a method is provided which consistently produces improved cell culture surfaces that generally avoid bare spots and possible undesired protein absorption or cell differentiation.

These and other features of the invention will be better understood through a study of the following detailed description and accompanying drawings.

DETAILED DESCRIPTION OF THE INVENTION

Figure 1:
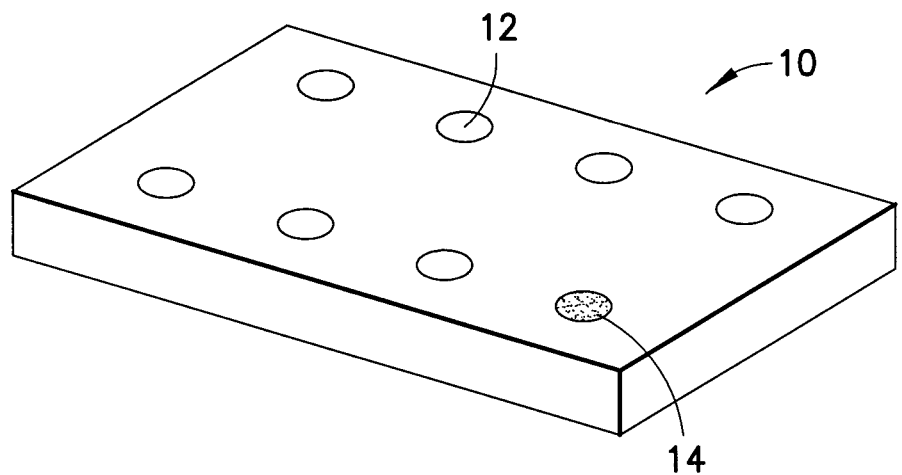
FIG. 1 depicts an improved cell culture surface found in accordance with the subject invention.

With reference to FIG. 1, a vessel 10 is shown, which initially includes an, untreated polymeric surface 12, which may be treated with the method herein to define an improved cell culture surface 14.

The polymeric surface 12 may be defined on a vessel 10 of any known configuration, such as a test tube, vial, flask, etc. Preferably, the polymeric surface 12 is the surface of a multiwell plate. For illustrative purposes, the vessel 10 shown in FIG. 1 is a multiwell plate. More preferably, the polymeric surface 12 is a surface of a well of a multiwell plate. It is further preferred that the multiwell plate conform to conventional multiwell plate standards (e.g., the Standards of the Society of Biomolecular Screening) so as to be usable in drug assay handling equipment (e.g., high throughput screening (HTS) equipment). The multiwell plate can be formed with any number or arrangement of wells (e.g., 96 (8×12) wells).

The term "polymeric surface" as used herein refers to any suitable such polymeric surface known to those skilled in the art. Suitable examples of polymeric surfaces include those obtained from polymeric hydrocarbons. As used herein, the term "polymeric hydrocarbon" is intended to refer to those polymers and copolymers obtained from repeating monomer units which are composed of carbon and hydrogen. The polymeric hydrocarbons may be saturated or unsaturated, and substituted or unsubstituted. Substituents may include atoms other than hydrogen and carbon, as long as they are present in an amount that does not detract from the substantially hydrocarbon nature of the polymer. Such substituents include acetal, halo, hydroxy, cyano, alkoxy, amino, amido, carbamoyl, and carbamido groups. Typical examples of a polymeric hydrocarbon surface include those made from substituted and unsubstituted polyethylene, polypropylene, polystyrene, ABS, PVC, polytetrafluoroethylene, polyvinylidene, and mixtures thereof. In a preferred embodiment, the polymeric hydrocarbon surface is polystyrene.

The term "polymeric surface" is also intended to include surfaces obtained from those polymers containing one or more heteroatoms such as oxygen, nitrogen, or sulfur, in addition to carbon and hydrogen. Typical examples of such polymeric surfaces include surfaces obtained from substituted and unsubstituted polyethers, polyesters, polyamides, polyamines, polyimines, polyurethanes, polyureas, polyacetals, polycarbonates, polyacrylates, polysulfides, polysulfones, and polysulfides. Also contemplated as being within the scope of the present invention are surfaces obtained from, polymers with backbones composed significantly of heteroatoms, such as silicones.

Figure 2:
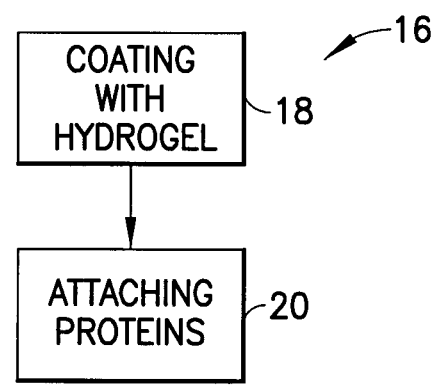
FIGS. 2-5 are flowcharts representing various aspects of the subject invention.

With reference to FIG. 2, a method 16 of the subject invention is depicted, which includes a step 18 of coating the polymeric surface 12 with a hydrogel, and a step 20 of attaching proteins to the coated surface. Any known technique can be used to conduct the step 18 of coating the polymeric surface 12 with a hydrogel. It is preferred that the hydrogel be coated so as to be immobilized on the polymeric surface 12. Preferably, the coating step 18 incorporates several intermediate steps as discussed below.

Figure 3:
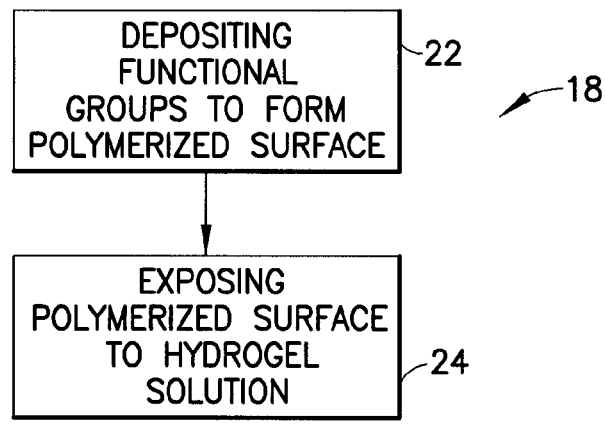

FIG. 3 depicts a preferred method of achieving the coating step 18 in the present invention. In a first step 22, functional groups are deposited on the polymeric surface 12. Thereafter, in a second step 24, the functional groups are exposed to hydrogel, preferably if) solution form. The functional groups may be any functional group desired, and preferably the functional groups are amine groups.

As will be recognized by those skilled in the art, the step 22 of depositing functional groups on the polymeric surface 12 may be achieved by several methods. By way of non-limiting examples, the step 22 may include plasma or corona discharge treatment, gamma irradiation, electron beam treatment, polymer absorption, evaporative deposition, plasma polymerization, self-assemble monolayer formation, or a combination thereof. Preferably, the depositing of the functional groups step 22 is performed by plasma treatment or corona discharge treatment.

Figure 4:
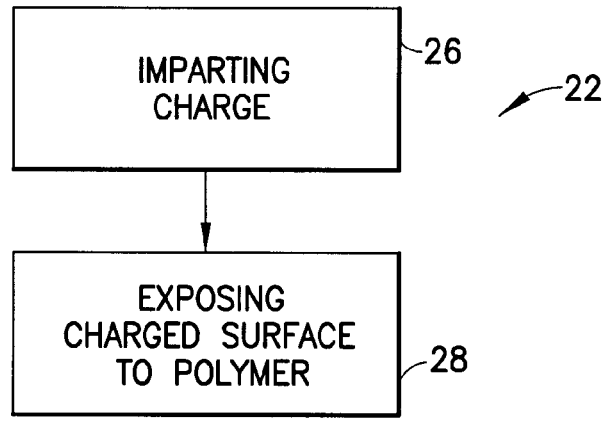

With reference to FIG. 4, in a preferred embodiment, the step 22 of depositing functional groups includes two separate steps. In a first step 26, a charge is imparted to the polymeric surface 12, to produce a charged polymeric surface. The charge may be any desired charge, although in a preferred embodiment, the charge is a negative charge. Once the polymeric surface 12 is charged, a second step 28 involves exposing the charged surface to a polymer to form a polymerized surface. In a preferred embodiment, the polymer is an amine-rich polymer. More preferably, the polymer is a positively charged poly-amine, such as polyethyleneimine or polylysine, and the polymer is exposed to the surface using a solvent, such as water. Similar means to treat polymeric surfaces are included in commonly-owned co-pending U.S. patent application, Ser. No. 11/496,933, the contents of which are hereby incorporated by reference.

The step 22 of depositing functional groups is complete once the polymeric surface 12 is exposed to the polymer to form a polymerized surface. Preferably, the resulting polymerized surface has a high density of functional groups. As stated above, the next step is the step 24 of exposing the polymerized surface to a solution of hydrogel. It is preferred that the hydrogel is in water solution or a buffered solution where the pH and ionic strength are suitable for a chemical reaction between the hydrogel and the functional groups oil the polymerized surface. It is understood that any hydrogel may be used with the present invention. Suitable hydrogels include polyvinyl alcohol, sodium polyacrylate, acrylate polymers and copolymers with an abundance of hydrophilic groups, polysaccharides and polysaccharide derivatives, such as dextran, and hyaluronan. It is preferred the hydrogel be stable and non-cytotoxic.

The step 24 of exposing hydrogel to the polymerized surface may be achieved by any known methods. Preferably, the step 24 results in the hydrogel being immobilized on the polymerized surface. Various techniques for immobilizing the hydrogel may be utilized. Preferably, to immobilize tie hydrogel, the hydrogel molecules are activated to produce reactive functional groups. Any functional groups may be obtained, which are reactive to the functional groups in the polymerized surface formed by the step 22. Preferably, the hydrogel molecules are activated to produce amine reactive groups. More preferably, a polysaccharide hydrogel, such as dextran, is oxidized with periodate to convert natural occurring hydroxyl groups to aldehyde groups. Periodate may be removed from the hydrogel solution by dialysis or column chromatography.

Once the hydrogel solution is prepared, the polymerized surface formed by the step 28 may be exposed to the reactively activated hydrogel as per step 24. In a preferred embodiment, the polymerized surface is an amine functionalized surface, and the activated hydrogel solution an amine reactive. As a result of the exposure, the reactive functional groups of the hydrogel solution become immobilized on the polymerized surface. In a preferred embodiment, oxidized polysaccharide hydrogel is immobilized on an amine polymerized surface. The immobilization may be achieved through any known mechanism Preferably, the immobilization is performed through the Schiff base formation between aldehyde and amine groups. The Schiff base can be stabilized by a reducing agent such as sodium borohydride ($NaBH_4$). Sodium borohydride also reduces the remaining aldehyde groups on the hydrogel to alcohol groups. This reduction step can be delayed until after the protein attachment step (step 20), so that the remaining aldehyde groups on the hydrogel can be used to react with the amine groups on the proteins.

Figure 5:
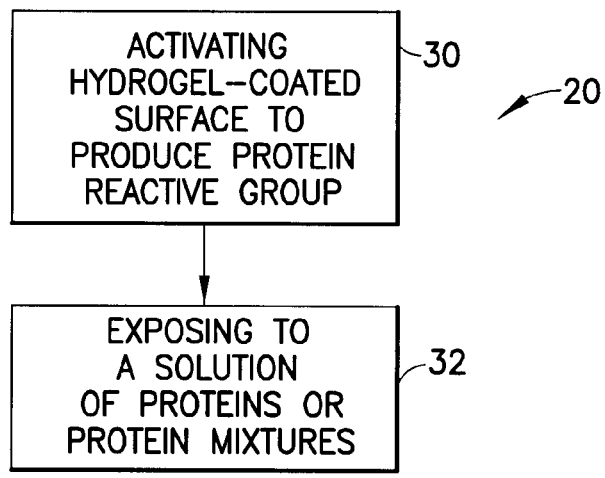

Once the step 18 is completed, with the polymeric surface 12 being coated with a hydrogel, as set forth above, the step 20 may be conducted to attach proteins to the hydrogel-coated surface. It is preferred that the proteins be attached so as to be immobilized on the hydrogel-coated surface. Proteins may be attached by any known technique. FIG. 5 depicts a preferred method of attaching proteins to the surface. Preferably, the proteins are attached in two steps. In a first step 30, the hydrogel-coated surface is activated to produce protein reactive groups. Any protein reactive group may be used, such as amine reactive groups, thiol reactive groups, carboxy reactive groups and the like. In a preferred embodiment, the hydrogel is activated to produce amine reactive groups. More preferably, the hydrogel has been activated to contain amine reactive groups before being immobilized on the polymerized surface; therefore further activation of the hydrogel is unnecessary. In a further preferred embodiment, the hydrogel may be an oxidized polysaccharide hydrogel, which has already been immobilized on the amine polymerized surface. In this further preferred embodiment, the hydrogel is further oxidized by periodate to enrich the aldehyde groups on the hydrogel surface.

In a second step 32, after the hydrogel surface has been activated, the activated hydrogel surface is exposed to a solution of proteins or protein mixtures resulting in attachment of the proteins or protein mixtures. Exposure of the proteins or protein mixtures to the hydrogel forms the cell culture surface 14. In a preferred embodiment, the proteins or protein mixtures have amine groups. The preferred proteins or protein mixtures have lysine and/or arginine residues on the surface, which provide the amine groups. The proteins or protein mixtures may be attached to the activated hydrogel surface through any known means. Preferably, the proteins or protein mixtures are covalently attached to the hydrogel surface. The covalent attachment may take place through the reaction of the amine-reactive groups on the hydrogel surface and the amine groups on the protein or protein mixture surface. In a more preferred embodiment, the proteins or protein mixtures are covalently attached to the oxidized polysaccharide hydrogel surface. Such attachment may take place through the Schiff base formation between the aldehyde group on the polysaccharide hydrogel surface and the amine groups on the protein surface. Optionally, as discussed above, an additional step may be added whereby the Schiff base is reduced, i.e., stabilized, with sodium borohydride, sodium cyano borohydride, or the like. The proteins or protein mixtures may include human fibronectin, human collagen, human vitronectin, human laminin, human entactin, and other extracellular matrix proteins and protein mixtures, and combinations thereof.

Figure 6:
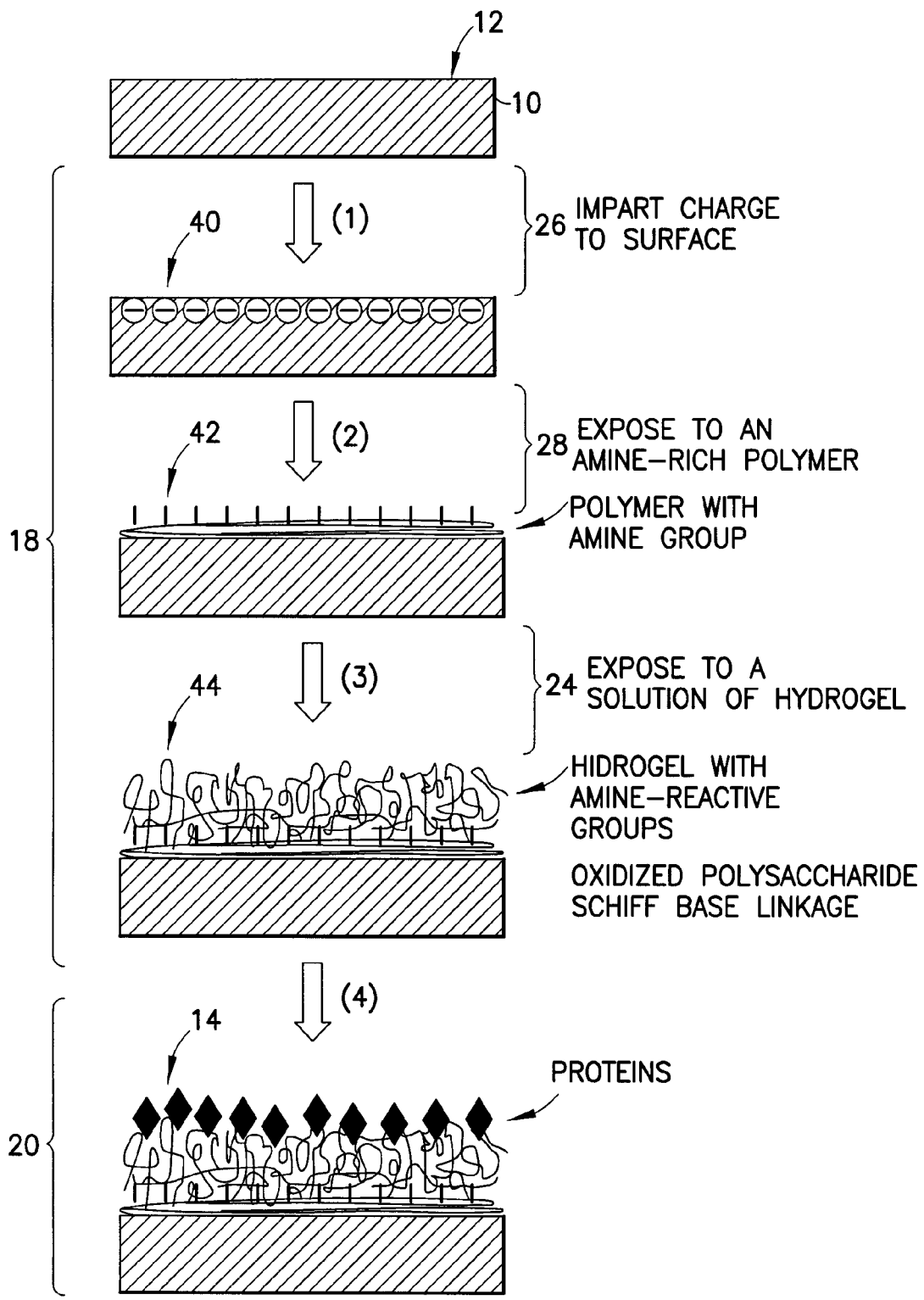
FIG. 6 is a flowchart representing an exemplary method in accordance with the subject invention.

With reference to FIG. 6, a preferred embodiment of the present invention is depicted. In this embodiment, the polymeric surface 12 of the vessel 10 is initially provided, the polymeric surface 12 being polystyrene. The step 18 of coating the polymeric surface 12 with hydrogel is initiated with the step 26, whereby a negative charge is imparted to the polymeric surface 12 by oxygen plasma treatment methods to produce a negatively charged surface 40. Thereafter, the step 28 is conducted by exposing the negatively charged surface 40 to a 1% solution of polyethyleneimine. Exposure to this solution forms a polymerized surface 42, more particularly an amine functionalized surface. Next, the polymerized surface 42 is exposed to a 20 mg/mL solution of oxidized dextran (hydrogel), to form a hydrogel coated surface 44, per the step 24. With the hydrogel coated surface 18 prepared, the step 20 of attaching proteins is conducted. The step 20 includes exposing the hydrogel coated surface 44 to a 10 mg/mL solution of periodate (step 30). Exposure to periodate further enriches the aldehyde groups on the surface of the vessel 10, thus activating the hydrogel coated surface 44. Thereafter, the activated hydrogel coated surface is exposed to a solution of proteins or protein mixtures (step 32) to form the cell culture surface 14. In a preferred embodiment, a protein mixture is used which contains 0.1 mg/mL of human fibronectin and 0.05 mg/mL human collagen.

The subject invention may have applicability in various contexts. By way of non-limiting examples, the subject invention can be used to prepare polymeric surfaces to obtain the following advantages: preservation of proteins on the surface by reducing the surface absorption-induced denaturing of proteins; prevention or reduction in the amount of proteins detaching from the surface; minimizing the non-specific absorption of proteins present in the cell culture medium, which therefore minimizes the risk of losing important components in cell culture medium; minimizing the undesired attachment of cells on bare surfaces. In stem cell culture, such advantages have a very important effect, as they may keep the cells from differentiation.

In a demonstration using the preferred embodiments of the present invention, mesenchymal stem cells were cultured in serum free media, on both a polystyrene surface prepared in accordance with the present invention (as described above in connection with FIG. 6) and a surface formed by passively coating an oxygen plasma treated polystyrene surface with the same protein mixture described above (i.e., 0.1 mg/mL of human fibronectin and 0.05 mg/mL human collagen). It was found that the number of cultured cells was six times greater on the surface of the present invention as compared to the surface formed by passive coating.

In another demonstration using the preferred embodiments of the present invention, it was found that human embryonic stem cells can be grown on the surface of the present invention in an undifferentiated state.

What is claimed is:

1. A method for treating a polymeric surface to define a cell culture surface for culturing mesenchymal stem cells or human embryonic stem cells thereon, the method comprising the steps of:
    a) coating the polymeric surface with a hydrogel consisting essentially of dextran, wherein said step of coating includes the steps of:
        i) depositing functional groups on said polymeric surface; wherein said functional groups are amines and
        ii) exposing said functional groups to a solution of hydrogel; and
    b) attaching proteins to said hydrogel coated surface;
    wherein said step of attaching proteins to said hydrogel-coated surface includes the steps of:
        i) activating said hydrogel-coated surface to produce at least one protein reactive group; and
        ii) exposing said hydrogel-coated surface to a solution of proteins or protein mixtures comprising human fibronectin and human collagen; and
    wherein said proteins or protein mixtures are covalently attached to the hydrogel-coated surface, thereby producing the cell culture surface for culturing mesenchymal stem cells or embryonic stem cells thereon wherein mesenchymal stem cells are cultured in greater number as compared to a cell culture surface formed by passive coating of said proteins and wherein human embryonic stem cells are cultured in an undifferentiated state.

2. The method of claim 1, wherein said step of depositing functional groups includes a method selected from the group consisting of plasma or corona discharge treatment, gamma irradiation, electron beam treatment, polymer absorption, evaporative deposition, plasma polymerization, self-assemble monolayer formation, or combinations thereof.

3. The method of claim 1, wherein said step of depositing functional groups includes the steps of:
    a) imparting a charge to the polymeric surface to produce a charged surface; and,
    b) exposing said charged surface to an amine-rich polymer.

4. The method of claim 3, wherein said charge is a negative charge.

5. The method of claim 1, wherein said solution of hydrogel is prepared by activating a hydrogel to produce secondary functional groups, said secondary functional groups being reactive with said functional groups.

6. The method of claim 5, wherein said activated hydrogel to produce said secondary functional groups is prepared by oxidizing a polysaccharide hydrogel with periodate.

7. The method of claim 1, wherein said protein reactive group includes one or more components selected from the group consisting of amine reactive groups, thiol reactive groups, carboxy reactive groups, and combinations thereof.

8. The method of claim 1, wherein said hydrogel is immobilized on said polymeric surface.

9. The method of claim 1, wherein said proteins or protein mixtures comprises 0.1 mg/ml human fibronectin and 0.05 mg/ml human collagen.

* * * * *

UNITED STATES PATENT AND TRADEMARK OFFICE
CERTIFICATE OF CORRECTION

PATENT NO. : 8,574,906 B2  Page 1 of 1
APPLICATION NO. : 12/188477
DATED : November 5, 2013
INVENTOR(S) : Xiaoxi Kevin Chen et al.

It is certified that error appears in the above-identified patent and that said Letters Patent is hereby corrected as shown below:

In the Specification:

Column 1, line 33, replace "Bare spots oil the surface..." with --Bare spots on the surface...--.

Column 2, line 58, replace "...preferably if) solution form." with --...preferably in solution form.--.

Column 3, line 40, replace "...to immobilize tie hydrogel..." with --...to immobilize the hydrogel...--.

Column 3, line 61, replace "...known mechanism  Preferably..." with --...known mechanism. Preferably...--.

Signed and Sealed this
Seventeenth Day of June, 2014

Michelle K. Lee
*Deputy Director of the United States Patent and Trademark Office*